(12) United States Patent
Kang et al.

(10) Patent No.: US 8,263,410 B2
(45) Date of Patent: Sep. 11, 2012

(54) METHOD AND APPARATUS FOR DETECTING METAL IONS, PROBE USED FOR THE SAME AND PREPARATION METHOD THEREOF

(75) Inventors: Taewook Kang, Seoul (KR); Luke P. Lee, Orinda, CA (US); Yeonho Choi, Albany, CA (US); Younggeun Park, Incheon (KR)

(73) Assignees: Industry-University Cooperation Foundation Sogang University, Seoul (KR); University of California, Berkeley, Berkeley, CA (US)

( * ) Notice: Subject to any disclaimer, the term of this patent is extended or adjusted under 35 U.S.C. 154(b) by 179 days.

(21) Appl. No.: 12/512,656

(22) Filed: Jul. 30, 2009

(65) Prior Publication Data

US 2011/0026024 A1 Feb. 3, 2011

(51) Int. Cl.
*G01N 21/47* (2006.01)
*G01N 30/20* (2006.01)

(52) U.S. Cl. ............... 436/73; 436/74; 436/80; 436/81; 436/84; 436/77; 436/82; 436/164; 356/337

(58) Field of Classification Search ............ 436/518, 436/528, 73, 164, 74, 80, 81, 84, 77, 82; 356/337
See application file for complete search history.

(56) References Cited

U.S. PATENT DOCUMENTS

| | | | | |
|---|---|---|---|---|
| 2005/0084908 | A1* | 4/2005 | Esaki ........................... | 435/7.1 |
| 2010/0196920 | A1* | 8/2010 | Lee et al. .................... | 435/7.1 |

OTHER PUBLICATIONS

W.R. Childs, et al., Large Area Patterning of Coinage-Metal Thin Films Using Decal Transfer Lithograpy. Langmuir 21, 195-202 (2005).
R.W. Tsien, et al., Calcium Channels, Stores, and Oscillations. Annu. Rev. Cell Biol. 6, 715-760(1990).
C.J. Chang, et al., A Tautomeric Zinc Sensor for Ratiometric Fluorescence Imaging: Application to Nitric Oxide-Induced Release of Intracellular Zinc. Proc. Natl. Acad. Soc. USA 101,1129-1134 (2004).
H. Bayraktar, et al. Facial Control of Nanoparticle Binding to Cytochrome c., J. AM. Chem. Soc. 129, 2732-2733 (2007).
C. Burda, et al. Chemistry and Properties of Nanocrystals of Different Shapes, Chem. Rev. 105, 1025-1102 (2005).
E. Coronado, et al., Reversible Colorimetric Probes for Mercury Sensing., J. Am. Chem. Soc. 127, 12351-12356(2005).
J.V. Ros-Lis, et al. A Regenerative Chemodosimeter Based on Metal-Induced Dye formation for the Highly Selective and Sensitive Optical Determination of $Hg^{2+}$ Ions. Angew. Chem. Int. Ed. 44, 4405-4407(2005).
X.J. Zhu, et al., A Near-Infrared-Fluorescent Chemodosimeter for Mercuric Ion Based on an Expanded Porphyrin, Angew. Chem. Int. Ed. 45, 3150-3154 (2006).
Fabrizio Mancin, et al., Self-Assembled Fluorescent Chemosensors, Chem. Eur. J. 12, 18844-1854 (2006).
R. Kramer, Fluorescent Chemosensors for $Cu^{2+}$ Ions: Fast, Selective, and Highly Sensitive. Angew. Chem. Int. Ed. 37, 772-773 (1998).

(Continued)

*Primary Examiner* — Robert J Hill, Jr.
*Assistant Examiner* — Dwan A Gerido
(74) *Attorney, Agent, or Firm* — Sughrue Mion, PLLC

(57) ABSTRACT

Disclosed is an innovative method for detecting metal ions based on selective plasmonic resonance energy transfer between metal-ligand complexes and a single nanoplasmonic particle as a probe. The selective plasmonic resonance energy transfer occurs if a resonance frequency matching condition between the single nanoplasmonic particle and the metal-ligand complexes is satisfied.

9 Claims, 7 Drawing Sheets

OTHER PUBLICATIONS

Y. Kim, et al., Gold Nanoparticle-based sensing of "Spectroscopically Silent" Heavy Metal Ions. Nano Lett. 1, No. 4, 165-167 (2001).

J. S. Lee, Colorimetric Detection of Mercuric Ion ($Hg^{2+}$) In Aqueous Media using DNA-Functionalized Gold Nanoparticles. Angew. Chem. Int. Ed. 46, 4093-4096 (2007).

G. L. Liu, et al., Quantized Plasmon Quenching Dips Nanospectroscopy Via Plasmon Resonance Energy Transfer, Nature Methods, vol. 4, No. 12, 1015-1017 (2007).

E. Gaggelli, et al., Copper Homeostasis and Neurodegenerative Disorders (Alzheimer's, Prion, and Parkinson's Diseases and Amyotrophic Lateral Sclerosis). Chem. Rev. 106, 1995-2044 (2006).

S. Jun, et al., The Aggregated State of Amyloid-β peptide in Vitro Depends on $Cu^{2+}$ Ion Concentration. Angew. Chem. Int. Ed. 46, 3959-3961 (2007).

X. Huang[a,b], et al. Cu(II) Potentiation of Alzheimer Aβ Neurotoxicity. J. Biol. Chem. 274, 37111-37116 (1999).

D.R. Brown, et al. The Cellular Prion Protein Binds Copper in Vivo. Nature 390, 684-687 (1997).

E.L. Que, et al., A Smart Magnetic Resonance Contrast Agent for Selective Copper Sensing J. Am. Chem. Soc. 128, 15942-15943 (2006).

Y. Zheng, et al., Development of Fluorescent Film Sensors for the Detection of Divalent Copper. J. Am. Chem. Soc. 125, 2680-2686 (2003).

G. Klein, et al., A Fluorescent Metal Sensor Based on Macrocyclic Chelation. Chem. Commun. 561-562 (2001).

Y. Choi, et al. Plasmon Resonance Energy Transfer (PRET)-based Molecular Imaging of Cytochrome $c$ in Living Cells. Nano Lett. 9, 85-90 (2009).

G.L. Liu, et al., A Nanoplasmonic Molecular Ruler for Measuring Nuclease Activity and DNA FootPrinting. Nature Nano. 1, 47-52 (2006).

G. Rascheke, et al., Biomolecular Recognition Based on Single Gold Nanoparticle Light Scattering. Nano Lett. 3, 935-938 (2003).

P. Andrew, et al. Energy Transfer Across a Metal Film Mediated by Surface Plasmon Polaritons. Science 306, 1002-1005 (2004).

R.P. Van Duyne, Molecular Plasmonics. Science 306, 985-986 (2004).

J. Zhao, et al. Resonance Surface Plasmon Spectroscopy: Low Molecular Weight Substrate Binding to Cytochrome P450. J. AM. Chem. Soc. 128, 11004-11005 (2006).

M. J. Romero, et al., Imaging of Resonant Quenching of Surface Plasmons by Quantum Dots. Nano Lett. 6, 2833-2837 (2006).

G.E. Fryxell, et al., Design and Synthesis of Selective Mesoporous Anion Traps. Chem. Mater. 11, 2148-2154 (1999).

J. Chaboy, et al., *Ab Initio* X-Ray Absorption Study of Copper K-edge XANES Spectra in CU (II) Compounds. Phys. Rev. B71, 134208-1-134208-7 (2005).

\* cited by examiner

METHOD AND APPARATUS FOR DETECTING METAL IONS, PROBE USED FOR THE SAME AND PREPARATION METHOD THEREOF

BACKGROUND

1. Field

This disclosure relates to a method and apparatus for detecting metal ions, a probe used for the same and a preparation method thereof.

2. Description of the Related Art

Optical absorption energy spectroscopy at visible wavelength range is a common analytical method in chemistry and biology since it has merits such as simplicity in measuring and data processing, wide usuage, non-tagged analysis, etc. Probes used in most optical systems so far have been developed primarily based on organic reporters which are detected by a change of color or fluorescence emission spectrum.

SUMMARY

Disclosed herein is in an embodiment a method for detecting metal ions including investigating whether plasmonic resonance energy transfer occurs between a single nanoplasmonic particle and metal-ligand complexes where the targeted metal ions are coordinated with ligands to form the metal-ligand complexes.

Disclosed herein is in an embodiment a probe for detecting metal ions being a single nanoplasmonic particle combined with ligands which are able to form metal-ligand complexes with the metal ions, wherein plasmonic resonance energy transfer occurs between the metal-ligand complexes and the single nanoplasmonic particle.

Disclosed herein is in an embodiment an apparatus for detecting metal ions including a single nanoplasmonic particle as a probe for detecting the metal ions, the single nanoplasmonic particle being combined with ligands which are able to form metal-ligand complexes with the metal ions, wherein plasmonic resonance energy transfer occurs between the metal-ligand complexes and the single nanoplasmonic particle.

Disclosed herein is in an embodiment a method for preparing a probe for detecting metal ions including: combining a single nanoplasmonic particle with ligands which are able to form metal-ligand complexes with the metal ions, wherein plasmonic resonance energy transfer occurs between the metal-ligand complexes and the single nanoplasmonic particle.

Plasmonic resonance energy transfers selectively from a single nanoplasmonic particle to metal-ligand complexes if a resonance frequency matching condition between the single nanoplasmonic particle and the metal-ligand complexes is satisfied, and to this end plasmonic resonance quenching occurs.

Using the selective plasmonic resonance energy transfer between metal-ligand complexes and a single gold nanoplasmonic particle, detecting a metal ion with a high sensitivity (for example, about 100 to about 1000 times more sensitive than organic reporter-based method) is possible. Furthermore, the detecting method may provide potentially nanoscopic temporal and spatial resolution as well as a high sensitivity (due to the large extinction coefficient) by shrinking the dimension of a detection site to a single nanoscale probe. Also, the detecting method may provide a target (i.e., metal ion to be detected) specific information and have compatibility with aqueous environments.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 2b schematically illustrates enlarged view of portion indicated as "a" in FIG. 2a.

DETAILED DESCRIPTION

Figure 1A:
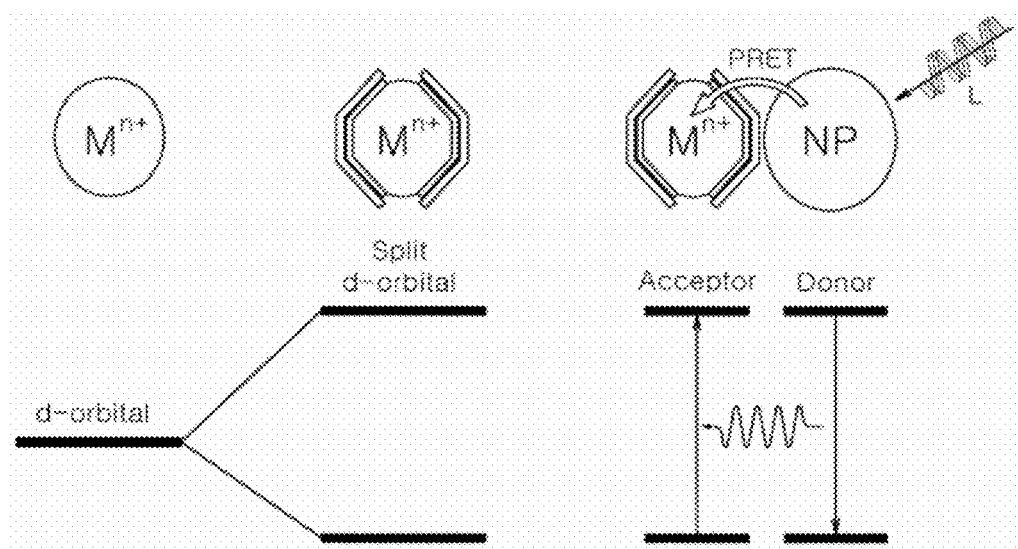
FIG. 1a is a schematic view illustrating a conception of nanoscopic detection of metal ions based on plasmonic resonance energy transfer between metal-ligand complexes and a single nanoplasmonic probe according to exemplary embodiments.

Exemplary embodiments are described more fully hereinafter. The invention may, however, be embodied in many different forms and should not be construed as limited to the exemplary embodiments set forth herein. Rather, these exemplary embodiments are provided so that this disclosure will be thorough and complete, and will fully convey the scope of the invention to those skilled in the art. In the description, details of features and techniques may be omitted to more clearly disclose exemplary embodiments.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "below", "lower", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly. The terminology used herein is for the purpose of describing particular embodiments only and is not intended to be limiting of the invention. As used herein, the singular forms "a," "an" and "the" are intended to include the plural forms as well, unless the context clearly indicates otherwise. Furthermore, the use of the terms a, an, etc. do not denote a limitation of quantity, but rather denote the presence of at least one of the referenced item. The terms "first," "second," and the like do not imply any particular order, but are included to identify individual elements. Moreover, the use of the terms first, second, etc. do not denote any order or importance, but rather the terms first, second, etc. are used to distinguished one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

In this context, a single nanoplasmon probe refers to a nano-sized (~100 μm) single metal particle which is able to show a surface plasmonic resonance.

In this context, a plasmonic resonance energy transfer means that when a nanoplasmonic particle is a donor of plasmonic resonance energy and a neighboring material is an acceptor of plasmonic resonance energy, plasmonic resonance energy transfers from the nanoplasmonic particle to the neighboring material.

In this context, a resonance energy quenching refers to partial or overall reduction of scattering light intensity in Rayleigh scattering spectrum of a nanoplasmonic particle via plasmonic resonance energy transfer. The partial reduction of scattering light intensity in Rayleigh scattering spectrum of a nanoplasmonic particle may refer to a spectralquenching dip where the scattering light intensity dips at some positions corresponding to absorption peak of a material to be detected. The overall reduction of scattering light intensity in Rayleigh scattering spectrum of a nanoplasmonic particle may refer to a spectral decrease.

Surface plasmonic resonance occurs when light is confined within a metal surface due to interaction with free-electrons in the metal. The surface plasmonic resonance may increase electromagnetic field on the surface of the metal. When materials such as particles or molecules (for example, metal ions, DNA, proteins etc.) are put around the surface of metal showing the surface plasmonic resonance, the surface plasmonic resonance and the materials affect each other.

That is, the neighboring materials may be affected as if they are exposed to a strong electromagnetic field. Meanwhile, the resonance feature of metal surface may show a delegate change due to a variation of dielectric function induced by the neighboring materials.

The conception used in the exemplary embodiments goes far beyond methods which focuses on a shift of resonance frequency in Rayleigh scattering spectrum where a shift of plasmonic resonance frequency resulting from the dielectric property of the nanoplasmonic particle's surroundings is investigated.

Instead, the exemplary embodiments are based on the investigation of resonant quenching of a single nanoplasmonic particle in connection with the formation of metal-ligand complexes.

Specifically, when the frequency of the electronic absorption band of metal-ligand complexes matches with the resonance frequency of the Rayleigh scattering of a single nanoplasmonic particle, plasmonic resonance energy can transfer from the single nanoplasmonic particle to the metal-ligand complexes. Accordingly, the plasmonic resonance energy transfer generates distinguishable spectralresonant quenching on the Rayleigh scattering spectrum of the single nanoplasmonic particle. Using the phenomenon, metals ions can be detected effectively (i.e. high sensitivity, high selectivity, target specific information acquirement, etc.).

Hereinafter, the exemplary embodiments will be described in detail with reference to the accompanying drawings. However, the aspects, features and advantages of the embodiments are not restricted to the ones set forth herein. The above and other aspects, features and advantages of the embodiments of the present invention will become more apparent to one of ordinary skill in the art to which the present invention pertains by referencing a detailed description given below. In the drawings, like reference numerals in the drawings denote like elements. The shape, size and regions, and the like, of the drawing may be exaggerated for clarity.

The underlying concept of the detection system for metal ions according to the exemplary embodiments is illustrated schematically in FIG. 1.

When metal ions (for example, the transition metal ions) binds with the matching ligand which is able to coordinate with the metal ions, metal-ligand complexes are formed and d-orbitals are split. Those split d-orbitals can generate a new absorption band of the metal-ligand complexes in visible range.

Surprisingly, due to the new absorption band occurring when the metal-ligand complexes are formed, Rayleigh scattering energy from a nanoplasmonic particle can be transferred to the metal-ligand complexes.

In other words, those split d-orbitals occurring when the metal-ligand complexes are formed allows the new absorption band in visible range. If a frequency of the new absorption band matches with the resonance frequency of the Rayleigh scattering of the nanoplasmonic particle, the plasmonic resonance energy can transfer from the nanoplasmonic particle to the metal-ligand complexes.

Due to the unique electronic transitions (e.g., d-d transition) of metal-ligand complexes, the metal-ligand complexes can generate a matched absorption band with Rayleigh scattering frequency of the single nanoplasmonic particle, meaning that those metal-ligand complexes are able to be acceptors in the plasmonic resonance energy transfer and the single nanoplasmonic particle is able to be a donor in the plasmonic resonance energy transfer.

Therefore, when the nanoplasmonic particle combined with ligands being able to form the metal-ligand complexes with the metal ions is put around the targeted metal ions, upon coordination of the metal ions with the ligands to form the metal-ligand complexes, the plasmonic resonance energy can transfer from the nanoplasmonic particle to the metal-ligand complexes as long as the frequency of the electronic absorption band of the metal-ligand complexes matches with the resonance frequency of the Rayleigh scattering of the nanoplasmonic particle.

The plasmonic resonance energy transfer can be confirmed from detecting the frequency matching. As well, the plasmonic resonance energy transfer can be confirmed by detecting spectralresonant quenching in Rayleigh scattering spectrum of the single nanoplasmonic particle. In other words, the plasmon energy transfer leads to the spectralresonant quenching in Rayleigh scattering spectrum of the single nanoplasmonic particle.

Figure 1B:
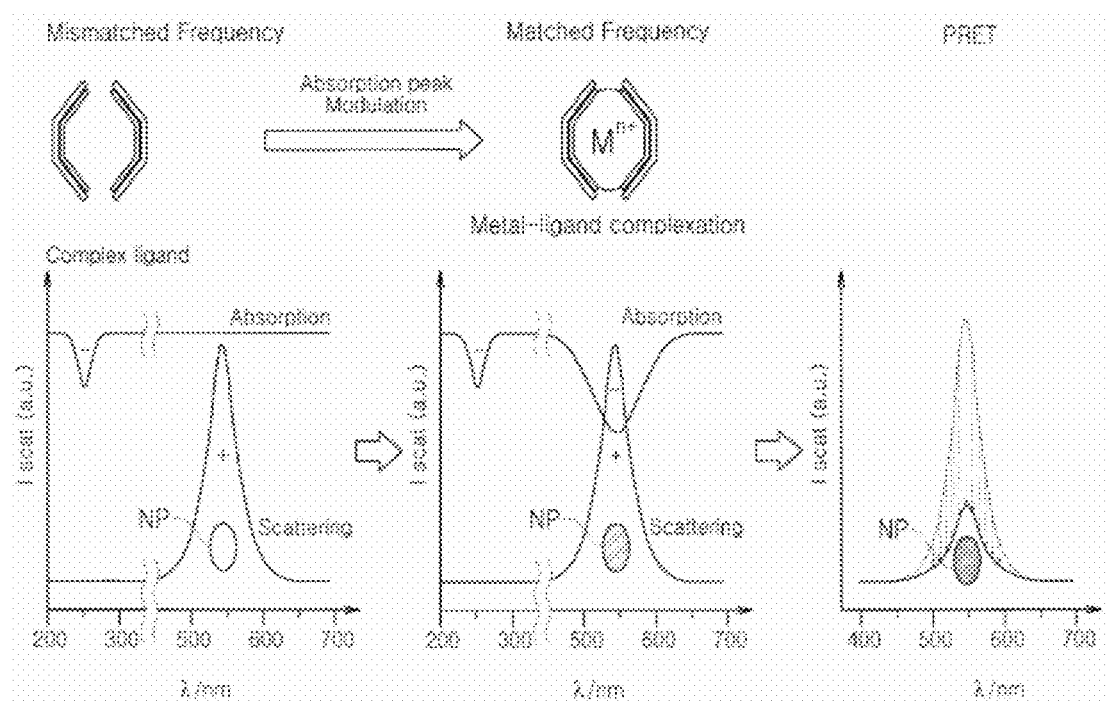
FIG. 1b shows that when the frequency of an electronic absorption band of metal-ligand complex matches with the frequency of resonant Rayleigh scattering of a nanoplasmonic particle, upon exposure of ligand-combined nanoplasmonic particle with targeted metal ions, the intentionally matched spectral overlap induces the selective energy transfer and generates distinguishable spectral resonant quenching on the resonant Rayleigh scattering spectrum of the nanoplasmonic particle.

FIG. 1b shows that when the frequency of an electronic absorption band of metal-ligand complex matches with the frequency resonant Rayleigh scattering of a nanoplasmonic particle, upon exposure of ligand-combined nanoplasmonic particle with targeted metal ions, the intentionally matched spectraloverlap induces the selective energy transfer and generates distinguishable spectralresonant quenching on the resonant Rayleigh scattering spectrum of the nanoplasmonic particle.

Referring to FIG. 1b, an initial mismatched frequency before metal-ligand complexes are formed changes to match with the frequency of resonant Rayleigh scattering of a nanoplasmonic particle after metal-ligand complexes are formed. When the frequency matches with the frequency of resonant Rayleigh scattering of a nanoplasmonic particle, the matched spectraloverlap between absorption peak and scattering light intensity spectrum induces the selective energy transfer and generates the spectralresonant quenching on the resonant Rayleigh scattering spectrum as shown in the right graph of FIG. 1b. In FIG. 1b, nanoplasmonic particle NP is schematically illustrated together with the change of Rayleigh scattering spectrum becomes darker as spectralresonant quenching occurs.

For reference, taken the color image of nanoplasmonic particle using a color CCD camera, it looks bright before the plasmon resonant quenching (refer to left NP schematically shown in FIG. 1b). However, the color image of nanoplasmonic particle becomes dark after the plasmon resonant quenching (refer to right NP schematically shown in FIG. 1b).

Figure 1C:
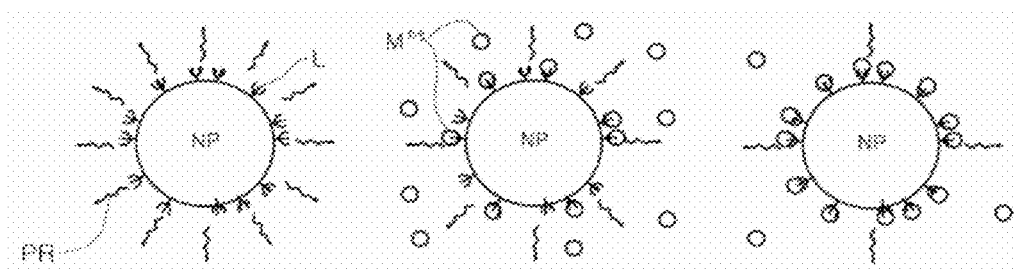
FIG. 1c shows that representative time-dependent changes of ligand-combined nanoplasmonic particle after exposure with metal ions with which the ligand is able to coordinate to form metal-ligand complexes.

FIG. 1c shows that representative time-dependent changes of ligand-combined nanoplasmonic particle after exposure with metal ions with which the ligand is able to coordinate to form metal-ligand complexes.

Referring FIG. 1c, a single nanoplasmonic particle NP is combined with ligand L. Herein, plasmonic resonance (PR) occurs actively. When NP is put around targeted metal ions M, ligand on NP can be coordinated with metal ions to form metal-ligand complexes. To this end, PR continuously diminishes and go away.

The exemplary embodiments are based on the plasmonic resonance energy transfer between the metal-ligand complexes and nanoplasmonic particle and the resulting resonance quenching.

Therefore, in an exemplary embodiment, a method for detecting metal ions includes detecting metal ions investigating whether plasmonic resonance energy transfer occurs between a single nanoplasmonic particle and metal-ligand complexes where the target metal ions are coordinated with ligands to form the metal-ligand complexes.

In the method, the metal ions may be detected by investigating whether the frequency of the absorption band of neighboring targeted materials occurring due to d-d transition is matched with the resonance frequency of the Rayleigh scattering of a plasmonic particle since the matching produces plasmonic resonance energy transfer.

Also, in the method, the metal ions may be detected by investigating plasmonic resonance quenching. The plasmonic resonance quenching is accompanied by the plasmonic resonance energy transfer. Herein, the plasmonic resonance quenching may be quantitized quenching dip or spectraldecreas depending upon the broadness of the absorption band of targeted resonant materials. That is, according to the broadness of absorption band of targeted metal ions, the plasmonic resonance quenching may be spectralquenching dip as well as spectral decrease.

In an exemplary embodiment, a probe for detecting metal ions may be a single nanoplasmonic particle physically and/or chemically combined with ligands which are able to form metal-ligand complexes with the targeted metal ions, wherein plasmonic resonance energy transfer occurs between the single nanoplasmonic particle and the metal-ligand complexes.

In an exemplary embodiment, a method for preparing the probe for detecting metal ions may include physically and/or chemically combining a single nanoplasmonic particle with the ligands which is able to form metal-ligand complexes with the targeted metal ions, wherein plasmonic resonance energy transfer occurring between the single nanoplasmonic particle and the metal-ligand complexes.

For example, the preparation of the probe may include immobilization of nanoplasmonic particles on substrate such as a glass slide, self-assembly of ligand on the surface of the particles.

In an exemplary embodiment, non-limiting examples of the nanoplasmonic particle may be gold or silver, and gold is preferred. Size or shape of the nanoplasmonic particle is not limited. As for the non-limiting examples, the nanoplasmonic particle may be a spherical shape, and the diameter of nanoplasmonic particle may be about 1 to about 100 nm. The diameter of nanoplasmonic particle may be about 20 to about 50 nm in order to secure enough scattering light intensity.

In an exemplary embodiment, non-limiting examples of the targeted metal ions may be $Cu^{2+}$, $Cd^{2+}$, $Zn^{2+}$, $Pt^{2+}$, $Hg^{2+}$, $Ni^{2+}$, $Co(II)$, $U(VI)$, $Pb(II)$ or other environmental polluting materials.

As for non-limiting examples, the targeted metal ion may be $Cu^{2+}$, and the ligand to form metal-ligand complex with the metal ion may be N-[3-(trimethoxysilyl)propyl]ethylenediamine (TMSen), 3-aminopropyltriethoxysilane (APTES), 6-aminohexane thiolhydrochloride (AHT), 2-aminoethane thiolhydrochloride (AET), NH2-Gly-Gly-His-COOH or NH2-(His)6-COOH.

As for non-limiting examples, the targeted metal ion may be $Cd^{2+}$, and the ligand to form metal-ligand complex with the metal ion may be phytochelatin, apo-metallothionein (apo-MT), ethylenediamine tetraacetic acid (EDTA) or chitosan.

As for non-limiting examples, the targeted metal ion may be $Zn^{2+}$, and the ligand to form metal-ligand complex with the metal ion may be phytochelatin, AgNt84-6 or chitosan.

As for non-limiting examples, the targeted metal ion may be $Pt^{2+}$, and the ligand to form metal-ligand complex with the metal ion may be 1,6-hexanedithiol (HDT).

As for non-limiting examples, the targeted metal ion may be $Ni^{2+}$, and the ligand to form metal-ligand complex with the metal ion may be NH2-Gly-Gly-His-COOH or NH2-(His)6-COOH.

As for non-limiting examples, the targeted metal ion may be $Hg^{2+}$, and the ligand to form metal-ligand complex with the metal ion may be 1,6-hexanedithiol (HDT), apo-metallothionein(apo-MT), poly(3-(3"-N,N,N-triethylamino-1"-propyloxy)-4-methyl-2,5-thiophene hydrochloride) (PMNT), AgNt84-6 or bis(ferrocenyl)azine.

As for non-limiting examples, the targeted metal ion may be Co(II), and the ligand to form metal-ligand complex with the metal ion may be diethylenetriamine pentaacetic acid (DTPA).

As for non-limiting examples, the targeted metal ion may be U(VI), and the ligand to form metal-ligand complex with the metal ion may be 2,9-dicarboxyl-1,10-phenanthroline.

As for non-limiting examples, the targeted metal ion may be Pb(II), and the ligand to form metal-ligand complex with the metal ion may be cyclohexyl-DTPA.

For reference, Table 1 shows the metal ions and the ligands to form metal-ligand complex with the metal ion.

TABLE 1

| Ligand | Targeted metal ions |
| --- | --- |
| phytochelatin | $Cd^{2+}$, $Zn^{2+}$ |
| 3-aminopropyltriethoxysilane (APTES) | $Cu^{2+}$ |
| N-[3-(trimethoxysilyl)propyl]ethylenediamine (TMSen) | $Cu^{2+}$ |
| 6-aminohexane thiolhydrochloride (AHT) | $Cu^{2+}$ |
| 2-aminoethane thiolhydrochloride (AET) | $Cu^{2+}$ |
| 1,6-hexanedithiol (HDT) | $Pt^{2+}$ |
| 1,6-hexanedithiol (HDT) | $Hg^{2+}$ |
| apo-metallothionein (apo-MT) | $Cd^{2+}$, $Hg^{2+}$ |
| poly(3-(3"-N,N,N-triethylamino-1"-propyloxy)-4-methyl-2,5-thiophene hydrochloride) (PMNT), | $Hg^{2+}$ |
| NH2-Gly-Gly-His-COOH or NH2-(His)6-COOH | $Cu^{2+}$, $Ni^{2+}$ |
| AgNt84-6 (metal-binding protein) | $Hg^{2+}$, $Zn^{2+}$ |
| bis(ferrocenyl) azine | $Hg^{2+}$ |
| ethylenediamine tetraacetic acid (EDTA) | $Cd^{2+}$ |
| diethylenetriamine pentaacetic acid (DTPA) | Co(II) |
| 2,9-dicarboxyl-1,10-phenanthroline | U(VI) |
| cyclohexyl-DTPA | Pb(II) |
| Chitosan | $Cd^{2+}$, $Zn^{2+}$ |

According to the exemplary embodiments, the probe for detecting metal ions is a nanoplasmonic particle physically and/or chemically combined with a ligand which is able to form metal-ligand complexes with metal ions. Herein, the method of combining with ligands may be a physical or chemical interaction (for example, covalent bonding).

Non-limiting examples may include immobilizing the nanoplasmonic particle on the substrate and the ligand to be able to form metal-ligand complexes are combined on the surface of the particle. Herein, the plasmon energy transfer can occur between the single nanoplasmon probe and the metal-ligand complexes.

According to the exemplary embodiments, the single nanoplasmon probe combined with specific ligands can work with high sensitivity and selectivity as a selective probe for detecting targeted metal ions.

Two features of the detecting technique according to the exemplary embodiments are considered to contribute to those remarkable selectivity or target specificity: exclusive complex formation only with the targeted metal ion, and plasmonic resonance energy transfer or plasmonic resonance quenching only occurring in the case of a frequency matching condition between the nanoplasmonic particle and the metal-ligand complex. That is, if the nanoplasmonic particle is physically and/or chemically combined (for example, covalently bonded) with ligands which are able to coordinate with the specific metal ion, and the ligand-combined nanoplasmonic particle (this can be also called as ligand-functionalized nanoplasmonic particle) is put around the targeted metal ions as a probe for detecting the targeted metal ions, then the ligand of the probe can exclusively form metal-ligand complexes with the targeted metal ions. Those formation of metal-ligand complexes can contribute to the selective detection of the metal ions. Also, the resonant quenching in Rayleigh scattering selectively occurs responding the specific metal ions. The resonant quenching results from the plasmon energy transfer between the metal-ligand complexes and the nanoplasmonic particle, which selectively occurs only if the frequency matches between the nanoplasmonic particle and metal-ligand complexes.

Furthermore, it is noteworthy that specific resonance frequency of a single nanoplasmonic particle combined with specific ligands could act as a selective probe for targeted metal ion with a high sensitivity and selectivity by providing the quantitative spectroscopic quenching information as a function of the local concentration of the target near the single probe, which has not been explored yet.

The examples and experiments will now be described. The following examples and experiments are for illustrative purposes only and not intended to limit the scope of the present invention.

[Experiment 1]

Example and Comparative Example

In this experiment, the detection technique according to the exemplary embodiments is applied to detect $Cu^{2+}$ in an aqueous solution. $Cu^{2+}$ has an analytical significance in biological and environmental processes. As shown below, through the detection technique, $Cu^{2+}$ can be detected with high sensitivity and selectivity.

The amine complex of $Cu^{2+}$ has optical absorption peaks in the visible range (around 550 nm) which coincides with the plasmonic resonance of the single gold nanoplasmonic particle used herein (i.e., resonance frequency matches).

The $Cu^{2+}$-ligand complex may be created by two equivalent ethylenediamine ligands [note that the log $K_1$ (association constant) for the ethylenediamine and $Cu^{2+}$ in solution is 10.75, while log $K_2$ is 9.28], exhibits a broad absorption band in the visible region centered at 547 nm with full width at half maximum (FWHM) of >90 nm.

Meanwhile, as for a nanoplasmon probe, a single gold nanoplasmonic particle is used.

The single gold nanoplasmonic particle used herein is 50 nm in diameter to ensure a sufficient intensity of light scattering, and composed of gold to allow for the binding of the ethylenediamine moiety (covalent bonding) on the surface to selectively recognize $Cu^{2+}$ in the aqueous solution.

Figure 2A:
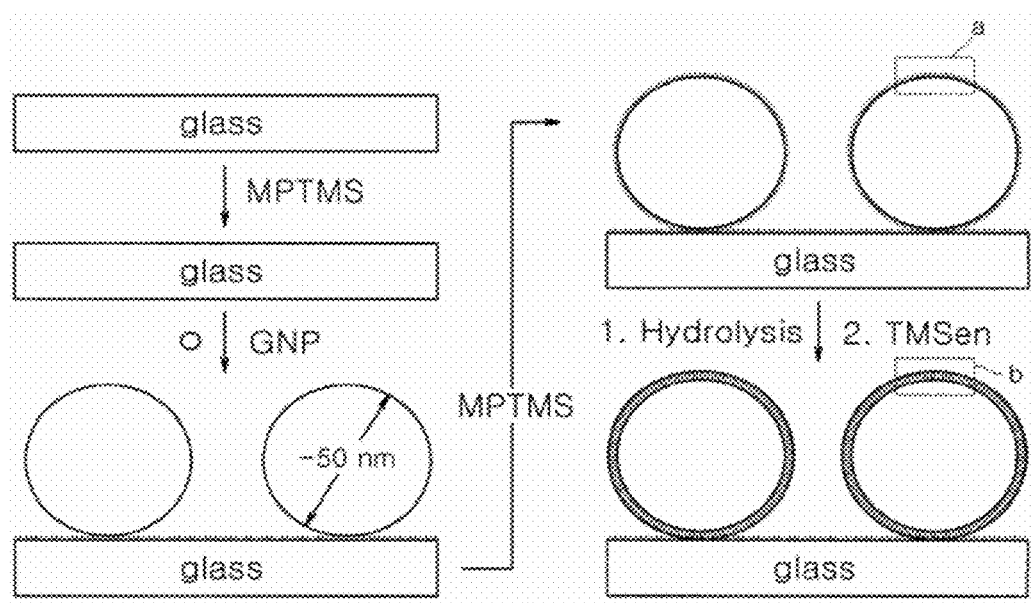
FIG. 2a schematically illustrates a preparation method of a gold nanoplasmon probe according to an example wherein a single gold nanoplasmonic particle is combined with ligands.
Figure 2B:
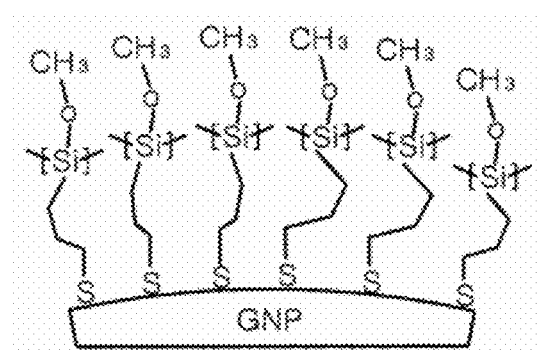
Figure 2C:
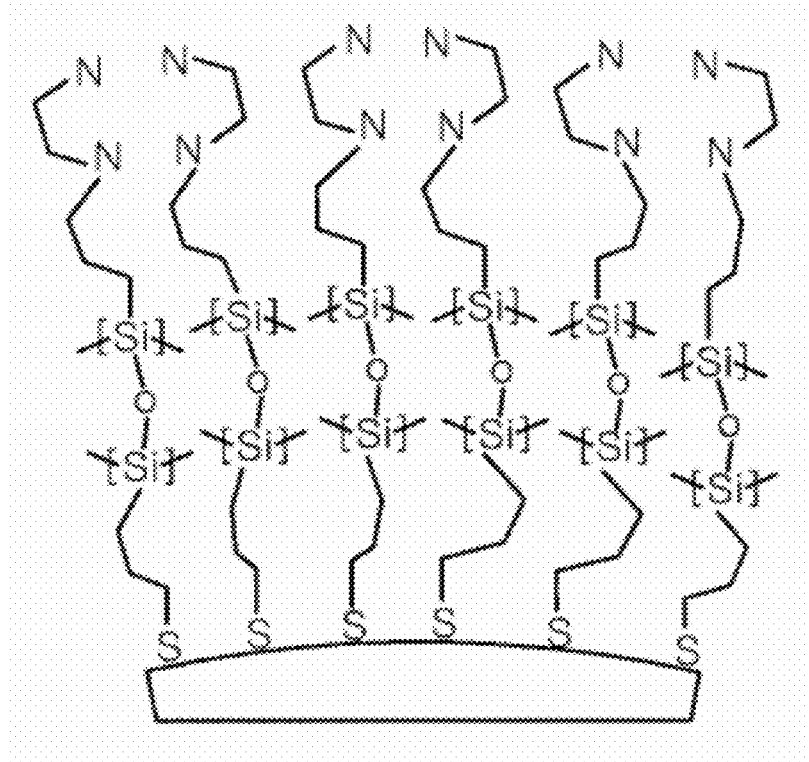
FIG. 2c schematically illustrates enlarged view of portion indicated as "b" in FIG. 2b.

FIG. 2a schematically illustrates a preparation method of a gold nanoplasmon probe according to the example wherein a single gold nanoplasmonic particle is combined with ligands. FIG. 2b schematically illustrates enlarged view of portion indicated as "a" in FIG. 2a. FIG. 2c schematically illustrates enlarged view of portion indicated as "b" in FIG. 2b.

Referring to FIG. 2, the probe according to example and comparative example may be prepared as follows.

Preparation of ethylenediamine-combined gold nanoplasmonic particle in example: Glass slides are cleaned in a piranha solution (30 min, for reference, the piranha solution is strong acidic oxidant and very harmful to personal contact so it should be carefully dealt with). A cleaned glass slide is modified with 3-mercaptotrimethoxysilane (MPTMS, Fluka) by incubation in 1 mM MPTMS isopropyl alcohol (IPA) for 24 h. The solution of MPTMS reacts with the surface of glass slide to form a surface presenting thiol groups. The glass slide is then rinsed with acetone and IPA. 50 nm spherical gold particles are immobilized on the MPTMS-modified glass slide (24 h, under mild sonication). Then freshly prepared particles on the glass slide were immersed into 1 mM MPTMS for 24 h. (refer to FIG. 2b which is an enlarged view of portion indicated as "a" in FIG. 2a). For hydrolysis of the methoxy groups of MPTMS, the silane-functionalized particles were then washed with ethanol and deionized water and immersed in a 0.1 M HCl solution for 1 h. Finally, the resulting gold nanoplasmonic particle on the glass were immersed into 1 mM N-[3-(trimethoxysilyl)propyl]ethylenediamine (TMSen) solution for 24 h, and ethylenediamine-combined gold nanoplasmonic particle is prepared (refer to FIG. 2c which is an enlarged view of portion indicated as "b" in FIG. 2a).

Preparation of gold nanoplasmonic particle without combination with the ethylenediamine ligand in comparative example: As comparison to the example, a gold nanoplasmonic particle without combination with the ethylenediamine ligand is prepared. Glass slides are cleaned in a piranha solution (30 min, for reference, the piranha solution is strong acidic oxidant and very harmful to personal contact so it should be carefully dealt with). A cleaned glass slide is modified with 3-mercaptotrimethoxysilane (MPTMS, Fluka) by incubation in 1 mM MPTMS isopropyl alcohol (IPA) for 24 h. The solution of MPTMS reacts with the surface of glass slide to form a surface presenting thiol groups. The glass slide is then rinsed with acetone and IPA. 50 nm spherical gold particles are immobilized on the MPTMS-modified glass slide (24 h, under mild sonication). Further combination process with the ethylenediamine ligands is not performed so as to obtain the gold nanoplasmonic particle without combination with the ethylenediamine ligands.

Scattering image and spectroscopy information may be acquired using a dark-field microscopy system with a true-color imaging charge-coupled device (CCD) camera, a spectrometer, etc.

Figure 3:
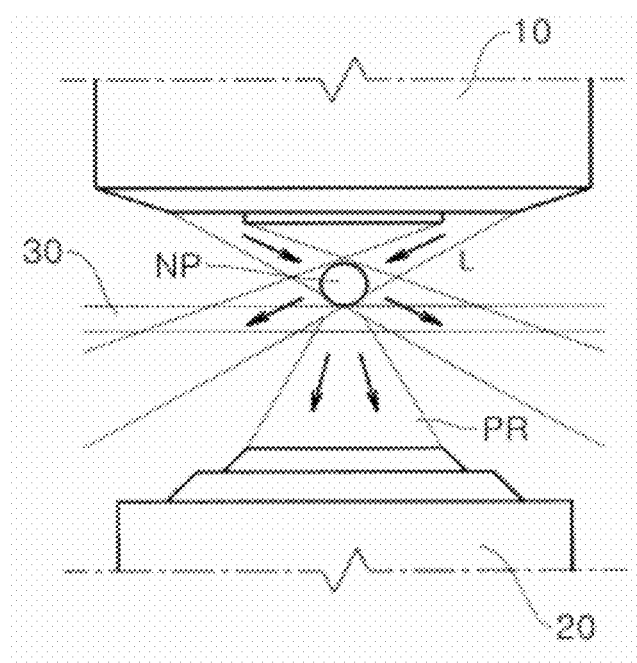
FIG. 3 schematically illustrates a microscopy system used in an example.

FIG. 3 schematically illustrates a microscopy system used in an example. The microscopy system consists of a Carl Zeiss Axiovert 200 inverted microscope (Carl Zeiss) equipped with a dark-field condenser (NA 1.2~1.4), a true-colour digital camera (CoolSNAP cf, Roper Scientific), and monochromator (300 mm focal length and 300 grooves per mm, Acton Research) with a 1024×256 pixel cooled spectrograph CCD camera (Roper Scientific). A 2-μm-wide aperture is placed in front of the monochromator to keep only a single gold nanoplasmonic particle in the region of interest.

Referring FIG. 3, white light L is illuminated from the dark field condenser lens 10 which is able to contact with liquid (buffer solution) to a single nanoplasmonic particle NP on substrate such as glass slide 30 having targeted metal ions contained in the liquid thereon, and then the scattering image is transferred to the objective lens 20. True-color imaging camera and/or spectrophotometer etc. (not shown) may be used ad connected to the objective lens 20.

Only a single gold nanoplasmonic particle showing the plasmonic resonance peak centered at 530~540 nm (typical FWHM bandwidth in the experiment is around 50 nm) with green colour is investigated. Aggregates, as judged by colour and scattering profile, are ruled out in the analyses.

Figure 4:
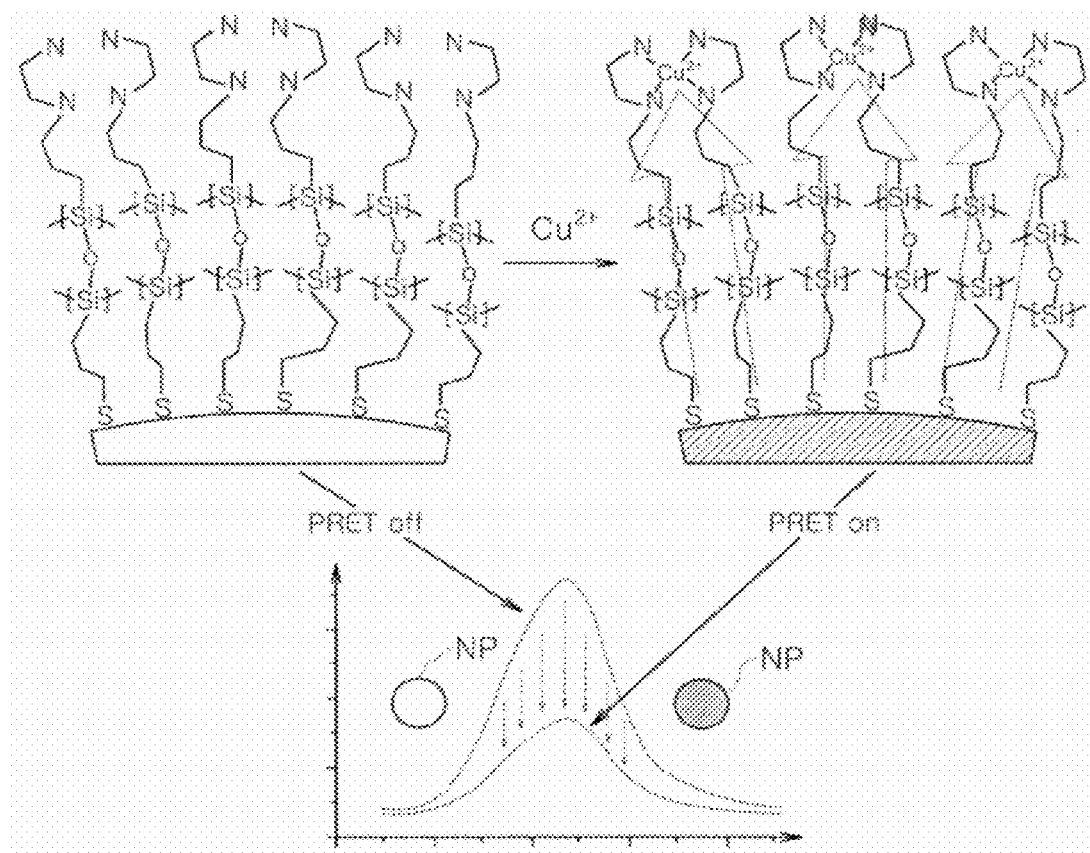
FIG. 4 schematically illustrates that ligand combined to a single gold nanoplasmonic particle is coordinated with metal ($Cu^{2+}$)) and metal($Cu^{2+}$))-ligand(amine based ligand) complexes [Cu(TMSen)$_2$]$^{2+}$ are formed to detect $Cu^{2+}$, together with a graph of expected Rayleigh scattering profile showing plasmonic resonance quenching (spectral decrease) via plasmonic resonance energy transfer between the single nanoplasmonic particle and resonant complexes [Cu(TMSen)$_2$]$^{2+}$.

FIG. 4 schematically illustrates that ligand combined to a single gold nanoplasmonic particle is coordinated with metal ($Cu^{2+}$) and metal($Cu^{2+}$)-ligand(amine based ligand) complexes $[Cu(TMSen)_2]^{2+}$ are formed to detect $Cu^{2+}$, together with a graph of expected Rayleigh scattering profile showing plasmonic resonance quenching (spectral decrease) via plasmonic resonance energy transfer between the single nanoplasmonic particle and resonant complexes $[Cu(TMSen)_2]^{2+}$. A coordination of $Cu^{2+}$ with ethylenediamine-functionalized gold nanoplasmonic particle leads to striking changes in the Rayleigh scattering profile.

Figure 5:
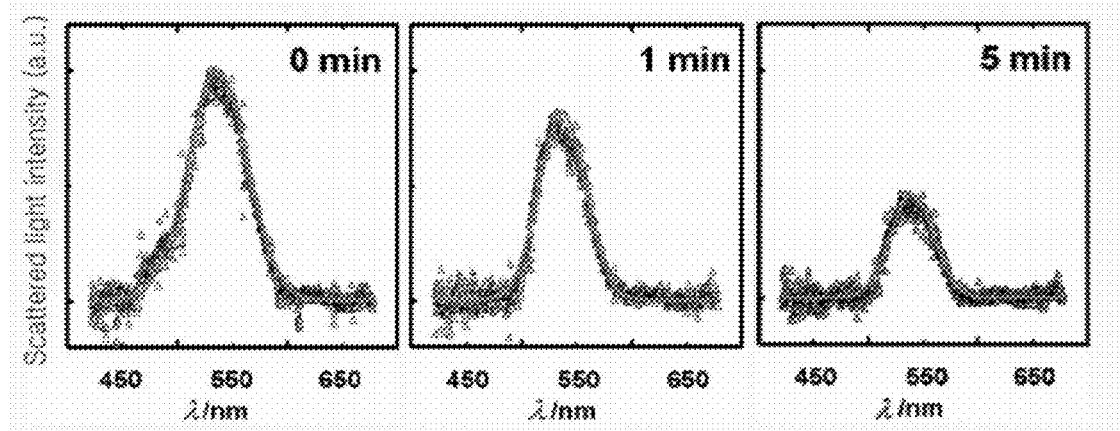
FIG. 5 is a graph showing a scattering spectrum of a gold nanoplasmonic particle as plasmonic resonance quenching occurs (0 minute, 1 minute, 5 minute) when detecting $Cu^{2+}$.

FIG. 5 is a graph showing a scattering spectrum of a gold nanoplasmonic particle as plasmonic resonance quenching occurs (0 minute, 1 minute, 5 minute) when detecting $Cu^{2+}$. Plasmonic resonance quenching occurs due to the plasmonic resonance energy transfer between the single nanoplasmon probe and metal-ligand complexes.

After 5 minutes of exposure to $Cu^{2+}$, metal-ligand complexes are formed as shown in FIG. 4, and the single gold nanoplasmonic particle exhibits a drastic decrease in scattered light intensity with concomitant decrease in dark-field transmittance without any noticeable spectralshift ($\Delta\lambda_{max}$) (refer to FIGS. 4 and 5).

Such significant spectral decrease without $\Delta\lambda_{max}$ cannot be explained by either a local refractive index change adjacent to gold nanoparticle or direct optical absorption by the conjugated $Cu^{2+}$ complexes. In fact, direct optical absorption by the conjugated complexes is several orders of magnitude too small to explain the observations. The optical absorption only accounts for <0.1% of scattered light intensity loss of the single gold nanoplasmonic particle even under the assumption of 100% excitation efficiency.

As established, the plasmonic resonance energy of a single gold nanoplasmonic particle can be transferred to surface $Cu^{2+}$ complexes. Thus, the sensing performance of the probe is investigated in detail. To evaluate the sensitivity, different concentrations of $Cu^{2+}$ from a single stock solution is tested. The selectivity of the probe is explored by testing the response of the probe to other biologically and environmentally relevant metal ions, including $Mg^{2+}$, $Ca^{2+}$, $Na^+$, $K^+$ etc. at a concentration range, for example, of about 100 nM to about 100 μM. As a result, the single gold nanoplasmon particle is confirmed to be able to detect $Cu^{2+}$ with high sensitivity and selectivity.

Due to both contributions of selective metal-ligand complex formation and the selective resonant quenching, a single gold nanoplasmon particle may show high selectivity for $Cu^{2+}$ over other metal ions such as $K^+$, $Na^+$, $Ca^{2+}$, $Mg^{2+}$, $Ni^{2+}$, and $Co^{2+}$. Significantly, this detection technique can in principle be extended to detect other metal ions by substituting another resonant metal-ligand pair or by modulating the particle plasmonic resonance positions.

Figure 6:
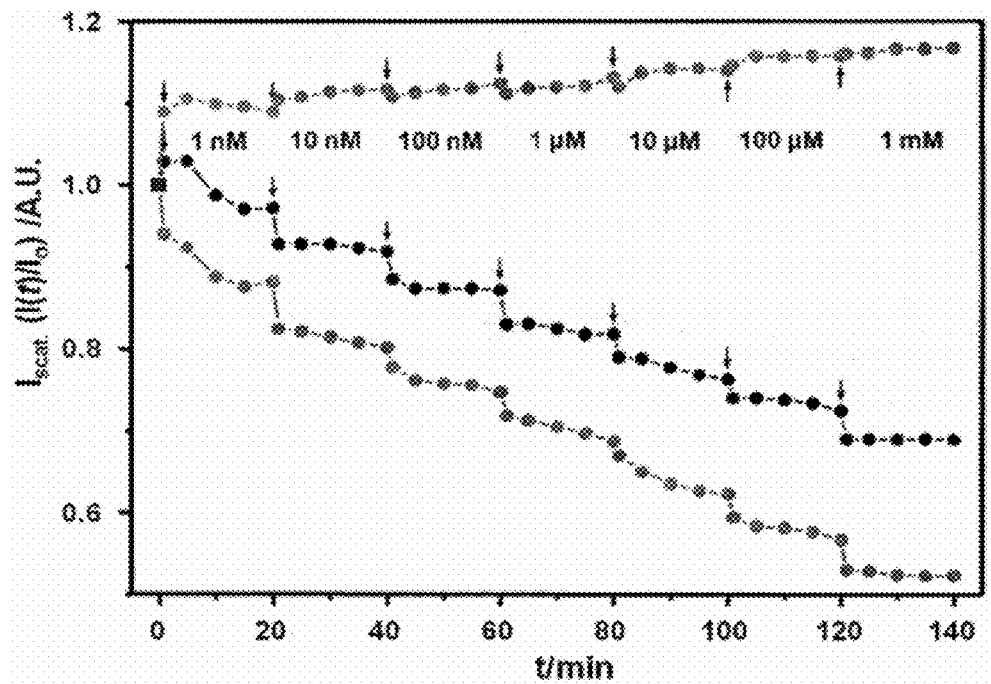
FIG. 6 is a graph showing normalized scattering light intensity as $Cu^{2+}$ concentration varies from about 1 nM to about 1 mM in order to show a real-time detection of $Cu^{2+}$.

FIG. 6 is a graph showing normalized scattering light intensity as $Cu^{2+}$ concentration varies from about 1 nM to about 1 mM in order to show a real-time detection of $Cu^{2+}$. That is, the normalized response of the particle to order-of-magnitude changes in $Cu^{2+}$ concentration is shown in FIG. 6.

Specifically, FIG. 6 shows plots of normalized scattering intensity at the scattering maximum ($\lambda_{max}$), $I(t)/I_o$ and versus time for an example of TMSen-combined gold nanoplamonic particle (middle dots in FIG. 6) and a compariative example of gold nanoplamonic particle without TMSen (upper dots in FIG. 6) for concentrations ranging from about 1 nM to about 1 mM. In FIG. 6, Y axis represents normalized scattering intensity at the scattering maximum ($\lambda_{max}$), $I(t)/I_o$ (arbitrary unit, $I_o$ is a scattering intensity at 0 minute, $I(t)$ is a scattering intensity at t minute), and X axis represents time (minute).

In FIG. 6, the relative scattering intensity at each $Cu^{2+}$ concentration for gold nanoplamonic particle of comparison example is subtracted from the relative scattering intensity for a TMSen-combined gold nanoplamonic particle in example to form the difference, providing a plot (lower dots in FIG. 6) of the net change in the relative scattering intensity, $\Delta I(t)/I_o$. Furthermore, the concentration values are indicated in FIG. 6. Arrows mark the points when solutions are changed. The square dot indicates the relative scattering intensity with DI water.

Referring to FIG. 6, the detecting technique is excellent in detecting metal ions at various concentrations of about 1 nM to about 1 mM.

In case of example (middle dots), the scattered light intensity of a single gold nanoplamonic particle decreases rapidly (~5 min) to a constant value upon addition of $Cu^{2+}$ solution, and the normalized scattering intensity ($I(t)/I_o$) at $\lambda_{max}$ shows a very similar systematic decrease with increasing $Cu^{2+}$ concentration. By stark contrast, the comparative example (upper dots) shows that addition of $Cu^{2+}$ solution to gold nanoparticles lacking ethylenediamine ligands does not produce a change in scattered light intensity except an 8.8±3.5% increase upon the first exposure to $Cu^{2+}$ solution.

Figure 7:
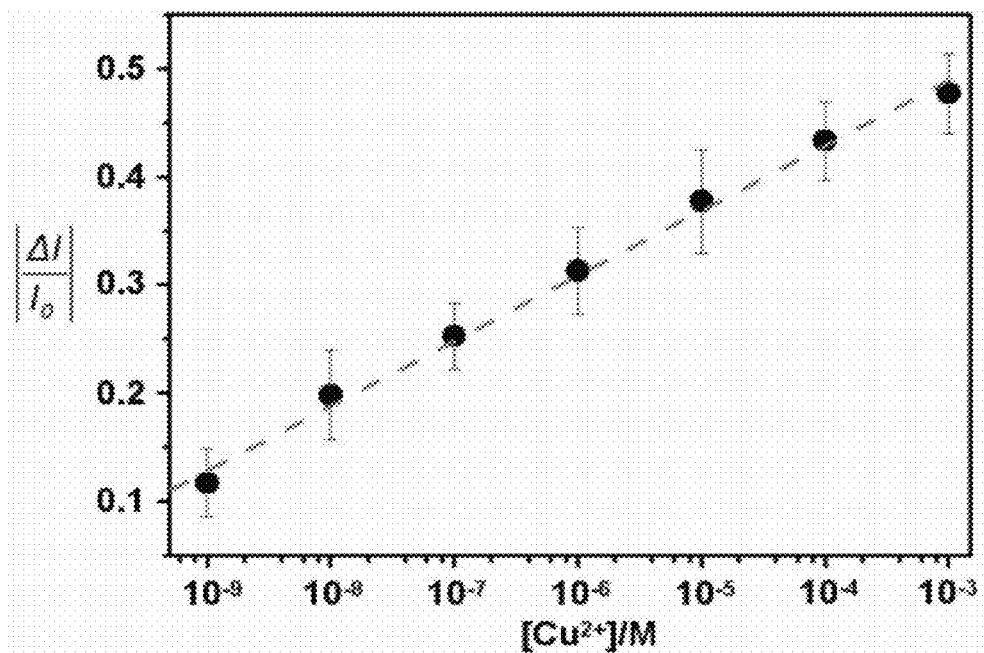
FIG. 7 is a graph showing a equilibrium differential scattering intensity change, $|\Delta I/I_o|$ (taken as absolute value for the sake of clarity; Y axis) as a function of $Cu^{2+}[(Cu^{2+}))/M$; X axis] concentration. The dashed line is a logarithmic fit to the $Cu^{2+}$ concentration data points. Error bars equals ±1SD. The regression coefficient ($R^2$) is 0.995.

FIG. 7 is a graph showing a equilibrium differential scattering intensity change, $|\Delta I/I_o|$ (taken as absolute value for the sake of clarity; Y axis) as a function of $Cu^{2+}[(Cu^{2+})/M$; X axis] concentration. The dashed line is a logarithmic fit to the $Cu^{2+}$ concentration data points. Error bars equals ±1SD. The regression coefficient ($R^2$) is 0.995.

Referring to FIG. 7, the regression coefficient in the $|\Delta I/I_o|-[Cu^{2+}]$ equilibrium curve is higher than 0.99 (semi-log scale) for a concentration range from 1 nM to 1 mM. It is noteworthy that a single gold nanoplasmon particle registers a substantial 11±3.1% scattered light intensity decrease after 5 min of exposure to 1 nM $Cu^{2+}$.

This response is significantly larger than the <1.0% drift in scattered light intensity of bare gold nanoplasmon particle of comparative example over 20 min. It is also noteworthy that the single gold nanoplasmon particle detects metal ions even at a concentration of 1 nM.

The detecting technique is about 100 to about 1,000 fold more sensitive than organic fluorophores, chromophore-based detection systems.

Moreover, the metal ions can be dissociated from the complexes, thus regenerating the gold nanoplasmon particle, by simply washing with acid (for example, washing with 1 M HCl for 1 h). This means that the detecting technique is also excellent in reuse.

Figure 8:
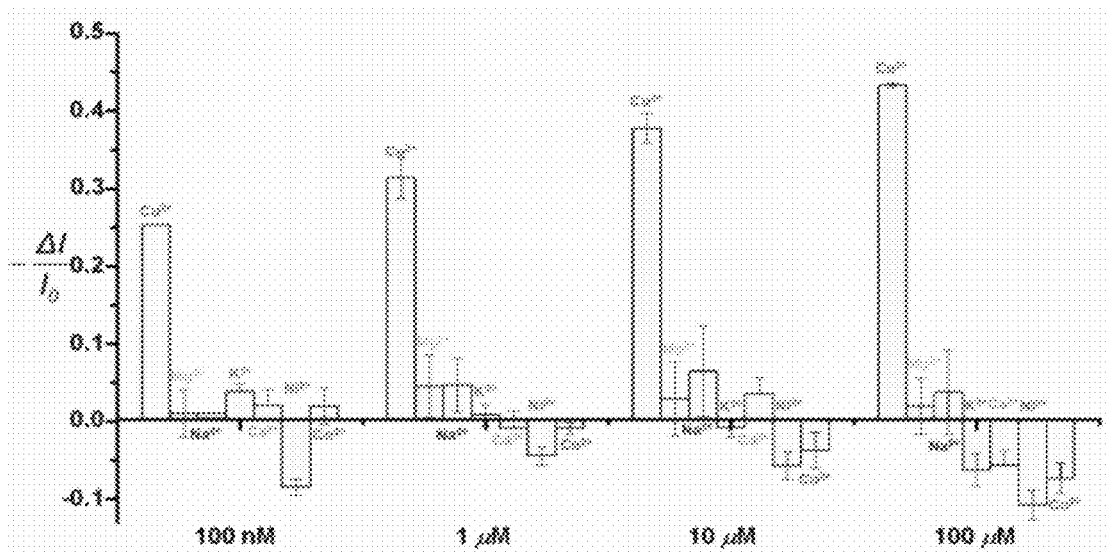
FIG. 8 is a graph showing a change in response of an example of TMSen-combined gold nanoplasmonic particle to environmentally and biologically relevant metal ions: $Cu^{2+}$, $K^+$, $Ca^{2+}$, $Mg^{2+}$, and $Na^+$, respectively and other transition metal ions: $Co^{2+}$ and $Ni^{2+}$. The height of each bar, $-\Delta I/I_o$ (Y axis) represents the percent change in the scattered light intensity following 20 min of metal ion exposure having respective concentration 100 nM, 1 μM, 10 μM, 100 μM (X axis).

FIG. 8 is a graph showing that $Cu^2$ is detected with high selectivity. Specifically, FIG. 6 shows a change in response of an example of TMSen-combined gold nanoplasmonic particle to environmentally and biologically relevant metal ions: $Cu^{2+}$, $K^+$, $Ca^{2+}$, $Mg^{2+}$, and $Na^+$, respectively and other transition metal ions: $Co^{2+}$ and $Ni^{2+}$. The height of each bar, $-\Delta I/I_o$ (Y axis) represents the percent change in the scattered light intensity following 20 min of metal ion exposure having respective concentration 100 nM, 1 μM, 10 μM, 100 μM (X axis).

The bar graph of FIG. 8 summarizes the sensing response to other metal ions. With the exception of $Cu^{2+}$, treatments of other metal ions with free ethylenediamine ligands generate no color change, nor are their respective absorbances in the UV-vis range. As expected, upon exposure to other metal ions, the probe according to example produces no discernable change in the scattered light intensity and $-\Delta I/I_o$ randomly fluctuates within at most 5% irrespective of concentration, suggesting that only a resonant metal-ligand complex with an absorption profile similar to the scattering spectrum of a single gold nanoplasmon particle can indeed be a receptor in the plasmonic resonance energy transfer process.

The additional experiments with $Co^{2+}$ and $Ni^{2+}$ also confirm the selectivity over other transition metal ions which form similar charge transfer complexes with the chelating ligands used due to the interaction of the d-orbital. As said before, those remarkable selectivity is credited with two key features of the detection technique: exclusive complex formation only with the targeted metal ion, and plasmon energy transfer only in the case of a frequency matching condition between the particle and the metal-ligand complex.

[Experiment 2]

In experiment 2, the probe according to example in experiment 1 is also tested to detect the changes in intracellular $Cu^{2+}$ in living HeLa cells.

Preparation of TMSen-combined gold nanoplasmonic particle for internalization into live cells (HeLa): First, 0.1 M MPTMS (20 μl) and 0.1M TMSen (20 μl) is dissolved in EtOH (1 ml) and 0.1M HCl (10 μl) is added for hydrolysis of the methoxy groups of MPTMS and TMSen. The mixture is stirred at room temperature for 1 hr in a PCR tube. Another solution containing 0.1 nM gold nanoplasmonic particle (50 nm, 1 ml) and 0.1M Tween-20 (20 μl) in a separate capped PCR tube is stirred at room temperature for 1 hr. The first solution (20 μl) is added to second one in a PCR tube and further stirred at room temperature for 24 hr. Excess MPTMS, TMSen, anions, TWEEN(polyoxyethylene sorbitan monolaurate), and reducing agents are removed from TMSen-combined gold nanoplasmonic particle probes by centrifugation for 30 min at 4,000 rpm for three times.

Cell culture: $CO_2$ independent media (Invitrogen inc.) supplemented with 10% [v/v] fatal bovine serum and 1% [v/v] penicillin is used. HeLa cells (~$10^6$ cells/dish) are counted, moves to a 2" cell culturing dish with 5 ml of media including approximately $10^9$ probes, and followed by the incubation at 37° C. in 5% $CO_2$ incubator for 24 h at least in order to internalize the probes into cells. To monitor the fluctuations of intracellular [$Cu^{2+}$] concentrations, media is replaced with 100 µM [$Cu^{2+}$] in PBS to remove uninternalized particles and induce the condition of copper ion exposure.

Copper ion detection via plasmonic resonance energy transfer in living cells: The HeLa cells with the probes is mounted on a Carl Zeiss Axiovert 200 inverted microscope. White light (Xenon Arc Lamp, Storzt 300 W) is illuminated to the cells only when the measurements are performed (integration time taken for spectra and dark field image are 0.2 s.) in order to avoid any thermal effect due to the long exposure time from the light source. Scattering spectra from the probes at different positions inside a single cell are collected with monochromator (300 mm focal length and 300 grooves per mm, Acton Research) with a 1024×256 pixel cooled spectrograph CCD camera (Roper Scientific).

As expected, upon exposure with 100 µM $Cu^{2+}$, the scattered light intensities collected from 30 different spots in a single cell represented a decrease.

This shows the detecting technique can be used effectively for detecting metal ions in living cells.

In conclusion, a highly selective and sensitive detection for metal ions can be obtained by exploiting the selective plasmonic energy transfer between the localized resonating plasmon kinetic energy Ep in a single gold nanoplasmon particle and the electronic transition energy in the metal-ligand complex. Furthermore, that nanoplasmonic probe according to the detection technique can detect low concentrations of $Cu^{2+}$ down to about 1 nM and produce quantitative spectroscopic quenching information as a function of the local concentration of the target near the single probe.

The detection technique can be applied to all fields requiring nanospectroscopy such as environmental monitoring, biology, cell (molecular) imaging in living cell, molecular analysis on a nano scale as well as micro scale, for example, scale in terms of size, concentration etc. The ability to resolve a single nanoparticle with a high sensing performance can be also used for the detection and visualization of metal ions in living systems.

While the invention has been shown and described with reference to certain exemplary embodiments thereof, it will be understood by those skilled in the art that various changes in form and details may be made thereto without departing from the spirit and scope of the invention as defined by the appended claims.

In addition, modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, wherein the metal ions are $Cu^{2+}$, and the ligands are at least one selected from the group consisting of N-[3-(trimethoxysilyl)propyl] ethylenediamine (TMSen), 6-aminohexane thiolhydrochloride (AHT), 2-aminoethane thiolhydrochloride (AET), $NH_2$-Gly-Gly-His-COOH and $NH_2$-(His)6-COOH.

2. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are $Cd^{2+}$, and the ligands are at least one selected from the group consisting of phytochelatin, apo-metallothionein (apo-MT), ethylenediamine tetraacetic acid (EDTA) and chitosan.

3. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are $Zn^{2+}$, and the ligands are at least one selected from the group consisting of phytochelatin, AgNt84-6 and chitosan.

4. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are $Pt^{2+}$, and the ligands are 1,6-hexanedithiol (HDT).

5. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are $Ni^{2+}$, and the ligands are at least one selected from the group consisting of $NH_2$-Gly-Gly-His-COOH and $NH_2$-(His)6-COOH.

6. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are $Hg^{2+}$, and the ligands are at least one selected from the group consisting of 1,6-hexanedithiol (HDT), apo-metallothionein(apo-MT), poly(3-(3"-N,N,N-triethylamino-1"-propyloxy)-4-methyl-2,5-thiophene hydrochloride) (PMNT), AgNt84-6 and bis(ferrocenyl) azine.

7. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are Co(II), and the ligands are diethylenetriamine pentaacetic acid (DTPA).

8. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are U(VI), and the ligands are 2,9-dicarboxyl-1,10-phenanthroline.

9. A method for detecting metal ions, comprising: investigating whether plasmonic resonance energy transfer occurs between a single nanoplasmonic particle and metal-ligand complexes where the targeted metal ions are coordinated with ligands to form the metal-ligand complexes, the metal ions are Pb(II), and the ligands are cyclohexyl-DTPA.

* * * * *